US 8,847,164 B2

(12) United States Patent
De Waele et al.

(10) Patent No.: US 8,847,164 B2
(45) Date of Patent: Sep. 30, 2014

(54) METHOD AND DEVICE FOR ONE-SHOT MEASUREMENT OF THE TRANSIENT BIREFRINGENCE INDUCED BY A PERTURBATION LYING WITHIN THE TERAHERTZ FREQUENCY RANGE

(75) Inventors: Vincent De Waele, Villaneuve d'Ascq (FR); Ulrich Schmidhammer, Paris (FR)

(73) Assignee: Centre National de la Recherche Scientifique and Universite Paris SUD 11, Paris (FR)

( * ) Notice: Subject to any disclaimer, the term of this patent is extended or adjusted under 35 U.S.C. 154(b) by 1080 days.

(21) Appl. No.: 12/808,597

(22) PCT Filed: Dec. 18, 2008

(86) PCT No.: PCT/FR2008/001783
§ 371 (c)(1),
(2), (4) Date: Oct. 15, 2010

(87) PCT Pub. No.: WO2009/106728
PCT Pub. Date: Sep. 3, 2009

(65) Prior Publication Data
US 2011/0019181 A1 Jan. 27, 2011

(30) Foreign Application Priority Data
Dec. 21, 2007 (FR) ...................................... 07 60296

(51) Int. Cl.
*G01J 5/02* (2006.01)
*G01N 21/35* (2014.01)
*G01N 21/23* (2006.01)
*G01N 21/17* (2006.01)

(52) U.S. Cl.
CPC ........ *G01N 21/3581* (2013.01); *G01N 21/1717* (2013.01); *G01N 21/23* (2013.01)
USPC ..................................................... 250/341.1

(58) Field of Classification Search
USPC ...................................................... 250/341.1
See application file for complete search history.

(56) References Cited

U.S. PATENT DOCUMENTS 6,724,783 B2 * 4/2004 Jalali et al. ......................... 372/9
7,928,390 B1 * 4/2011 Zhuang et al. ............ 250/339.08

(Continued)

OTHER PUBLICATIONS

G. Berden Et Al: "Time Resolved Single-Shot Measurements of Transition Radiation at the Thz Beamline of Flash Using Electro-Optic Spectral Decoding"; Proceedings of Epac 2006, [Online] 2006, pp. 1058-1060, XP002490371 Edinburgh, Scotland; Retrieved from the Internet:<URL:http://www.rijnhuizen.nl/users/gielber>; den/pdfs/EPAC2006_TUPCH027.pdf>[retrieved on Jul. 30, 2008] p. 1058, col. 2, line 10-p. 1059, col. 2, line 20; figures 1, 2.

(Continued)

*Primary Examiner* — David Porta
*Assistant Examiner* — Mindy Vu
(74) *Attorney, Agent, or Firm* — Blank Rome LLP (57) ABSTRACT

The present invention relates to a method and a device for direct, non-deformed one-shot measurement of the transient birefringence induced in an optical medium by a perturbation lying within the terahertz frequency range. The aim of the present invention is to alleviate the drawbacks of the prior art by providing a one-shot measurement method and a one-shot measurement device, these being based on the spectral encoding/decoding principle, which are compatible with all short pulse (UV-NIR) laser sources. In this regard, the invention provides a one-shot method for measuring the transient birefringence induced in an optical medium (12) by at least one terahertz perturbation (6), the method including a step of transmitting and spectrally encoding a pulsed optical signal (2). The encoding step, which includes the generation of a supercontinuum (3), is furthermore combined with a step of decoding the polarization ellipticity of the supercontinuum, induced by the perturbation (6) of the medium (12), by decomposing the electric field of the supercontinuum in two polarization directions and simultaneously measuring the intensities Is and Ip of the two components.

21 Claims, 4 Drawing Sheets

(56) References Cited

U.S. PATENT DOCUMENTS

2002/0067480 A1* 6/2002 Takahashi ............... 356/317
2005/0230625 A1* 10/2005 Zhang et al. ............... 250/341.1

OTHER PUBLICATIONS

Yan X et al: "Subpicosecond electro-optic measurement of relativistic electron pulses"; Physical Review Letters Aps USA,• [Online] vol. 85, No. 16, Oct. 16, 2000, pp. 3404-3407, XP002490736 ISSN: 0031-9007; Retrieved from the Internet: URL:http://prola.aps.org/pdf/PRL/v85/i16/p 3404_1>[retrieved on Jul. 31, 2008] p. 3404-3405; figures 1-3.

J.-L. Marignier et al: "Time-resolved spectroscopy at the picosecond laser-triggered electron accelerator Elyse" Radiation Physics and Chemistry Elsevier UK, vol. 75, No. 9, Sep. 2006; pp. 1024-1033, XP002490591; ISSN: 0969-806X p. 1025, col. 1, line 14-col. 2, line 28; figures 1, 9.

Kartazaev V et al: "Polarization properties of SC generated in CaF2" Optics Communications Elsevier Science B.V. Netherlands, [Online] vol. 281, No. 3, Oct. 28, 2007; pp.; 463-468, XP002490590, Online ISSN: 0030-4018; Retrieved from the Internet: URL: http://www.sciencedirect.com/science?_ob=ArticleURL&_udi=B6TVF-4PXMWJV-2&_user=987766&_rdoc=1&_fmt=&_orig=search&_sort=d&view=c&_acct=C000049880&_version=1&_urlVersion=0&_userid=987766&md5=ee3ba0dda2bc606cef7734352318cdd5>[retrieved on Jul. 31, 2008]p. 463, col. 2, line 2-p. 465, col. 2, line 11; figures 1-5.

Berden G et al: "Benchmarking of electro-optic monitors for femtosecond electron bunches"; Physical Review Letters American Physical Society USA, [Online]; vol. 99, No. 16, Oct. 19, 2007, pp. 164801-1, XP002490369; ISSN: 0031-9007 Retrieved from the Internet: <URL:http://www.rijnhuizen.nl/users/gielber>; den/pdfps//Berden_PRL_2007.pdf>° Retrieved on Jul. 30, 2008]pp. 164801-1, col. 1, line 33 pages; 164801-4, col. 1, line 22; figures 1-4.

Jingling Shen et al: "Electron-beam bunch length monitor based on electro-optic detection technique"; Proceedings of the Spie—The International Society for Optical Engineering Spie—The International; Society for Optical Engineering USA,vol. 5646, No. 1, Jan. 28, 2005, pp. 269-274, XP002490592; ISSN: 0277-786X; paragraph [001.].

G. Phillips et al: "Single Shot Longitudinal Bunch Profile Measurements by Temporally Resolved Electro-Optical Detection" Proceeedings of the 8th European Workshop on Beam Diagnostics and Instrumentation; (DIPAC 2007), Venice, Italy, [Online] May 23, 2007, pp. 1-3, XP002490374 online pre-press release; Retrieved from the Internet: URL:http://felino.elettra.trieste.it/papers/WE02A02.pdf> [Retrieved on Jul. 30, 2008] p. 1; figures 1-3.

Wilke I et al: "Single-shot electron-beam bunch length measurements" Physical Review Letters Aps USA, [Online] vol. 88, No. 12, Mar. 25, 2002, pp. 124801-1-124801-4, XP002490373, ISSN: 0031-9007 Retrieved from the Internet: URL:http://prola.aps.org/pdf/PRL/v88/i12/e124801> [retrieved on Jul. 30, 2008] pp. 124801-2, col. 1, line 5-line 46.

L. Duvillaret, S. Rialland, J.-L. Coutaz, J. Opt. Soc. Am. B 19, 2692 (2000).

J. A. Valdmanis, G. Mourou. IEEE J. Quantum Electron. 22, 69 (1986).

Z. Jiang, X.-C. Zhang. Appl. Phys. Lett. 72, 1945 (1998).

F. G. Sun, Z. Jiang, X.-C. Zhang. Appl. Phys. Lett. 73, 2233 (1998).

J. R. Fletcher. Opt. Exp. 10, 1425 (2002).

B. Yellampalle, K. Y. Kim, G. Rodriguez, J. H. Glownia, A. J. Taylor. Appl. Phys. Lett. 87, 211109 (2005).

K. Y. Kim, B. Yellampalle, G. Rodriguez, R. D. Averitt, A. J. Taylor, J. H. Glownia, Appl. Phys. Lett., 88, 041123 (2006).

J. Shan, A. S. Weling, E. Knoesel, L. Bartels, M. Bonn, A. Nahata, G. A. Reider, T. F. Heinz. Opt. Lett. 25, 426 (2000).

S. P. Jamison, J. Shen, A. M. MacLeod, W. A. Gillespie, D. A. Jaroszynski. Opt. Lett. 28, 1710 (2003).

K. Y. Kim, B. Yellampalle, A. J. Taylor, G. Rodriguez, J. H. Glownia. Opt. Lett. 32, 1968 (2007).

Z. Jiang, F. G. Sun, Q. Chen. Appl. Phys. Lett. 74, 1191 (1999).

Y. Li. Appl. Phys. Lett. 88, 251108 (2006).

S. P. Mickana, K.-S. Leeb, T- M. Lub, J. Munch, D. Abbotta, X.-C. Zhang. Microelectronics Journal 33, 1033 (2002).

* cited by examiner

METHOD AND DEVICE FOR ONE-SHOT MEASUREMENT OF THE TRANSIENT BIREFRINGENCE INDUCED BY A PERTURBATION LYING WITHIN THE TERAHERTZ FREQUENCY RANGE

REFERENCE TO RELATED APPLICATIONS

The present application is the U.S. national phase of PCT/FR2008/001783, filed on Dec. 18, 2008, and published as WO 2009/106728 A1 on Sep. 3, 2009, which claims benefit to French Patent Application No. 0760296, filed Dec. 21, 2007, whose disclosures are hereby incorporated by reference in their entireties into the present disclosure.

FIELD OF THE INVENTION

The present invention concerns a device for the direct, non-deformed, one-shot measurement of the transient birefringence induced in an optical medium by a perturbation lying within the terahertz frequency range.

The invention concerns the technical field of the characterisation of the birefringence induced in an optical medium and more particularly the electro-optical or magneto-optical diagnostic field. In this regard, the invention applies in particular to terahertz spectroscopy, to the characterisation of electronic components and to the diagnosis of beams of charged and accelerated particles.

DESCRIPTION OF RELATED ART

The conventional sampling method for characterising the temporal profile of terahertz radiations is based on the Pockels effect. The characterisation method thus consists of passing a pulsed optical signal, referred to as the sensor pulse signal, through an optical medium, at a point subjected to terahertz radiation. Thus the electrical field of the sensor pulse undergoes a phase delay, along the two axes of the induced birefringence. The temporal profile of the terahertz radiation can then be reconstituted from knowledge of the temporal variation in the phase delay obtained, for example by modulation of the polarisation of the electromagnetic field of the sensor pulse signal as a function of time (L Duvillaret, S Rialland, J-L Coutaz, J Opt. Soc. Am. B 19, 2692 2000)).

Conventional electro-optical sampling is based on the repetition of the signal to be measured. The temporal profile of terahertz radiation is reconstituted from sequential acquisitions obtained by varying the time delay between the terahertz radiation and an ultra-short sensor laser pulse. The electro-optical sampling devices based on this technique can achieve sub-picosecond temporal resolutions, and are sensitive over several orders of magnitude, thanks to the use of high repetition rate (MHz) laser sources coupled to a synchronous amplifier, or "lock-in amplifier" (J A Valdmanis, G Mourou, IEEE J Quantum Electron. 22, 69 1986).

Nevertheless, for many applications, the technique described above is not applicable, in particular in the case of applications relating to the characterisation of unstable systems (biological samples, reactive physico-chemical systems, imaging of moving or unstable objects), or in the case of experiments with inherent shot by shot fluctuations. Thus, in some configurations, the terahertz radiation cannot be precisely synchronised with the sensor pulses. In other cases, the fluctuations in this terahertz radiation are specifically characterised with respect to a reference optical clock.

For these many cases, not covered by conventional electro-optical sampling, methods for the single-shot recording of the temporal profile of terahertz radiation have been developed.

Historically, the first single-shot acquisition method proposed consists of encoding the temporal profile of terahertz radiation on the spectrum of a sensor laser pulse stretched in time, by frequency drift. The terahertz pulse is then decoded by dispersing the sensor pulse in a spectrograph, by virtue of the knowledge of the time-frequency dispersion relationship. Spectral encoding/decoding is then spoken of (Z Jiang, X-C Zhang, Appl. Phys. Lett. 72, 1945 1998; X-C Zhang, Z Jiang, U.S. Pat. No. 6,573,700 2003).

In this single-shot measurement scheme, the temporal resolution and the width of the detection window are linked by the spectral width of the sensor pulse signal. This is a limit intrinsic to this encoding/decoding principle. It is thus accepted that a measurement of the temporal resolution of the device is given by the following equation (F G Sun, Z Jiang, X-C Zhang, Appl. Phys. Lett. 73, 2233 1998; J R Fletcher, Opt. Exp. 10, 1425 2002):

$$T_{Min} = \sqrt{T_o \cdot T_c}, \text{ where}$$

$T_{min}$ is the measurement of the temporal resolution;
$T_o$ is the duration of the sensor pulse limited by Fourier transformation;
$T_c$ is the duration of the stretched sensor pulse.

To overcome the limit described above, many efforts have been made, in particular with a view to the characterisation of pulses of accelerated particles, in order to develop devices with a higher temporal resolution. Novel methods have thus been proposed:

Interferometric decoding, which decodes the induced birefringence information inscribed on the stretched spectrum of the optical sensor from an interference figure. This method is indirect because of the necessity to reconstitute the temporal profile from a complex algorithm (B Yellampalle, K Y Kim, G Rodriguez, J H Glownia, A J Taylor, Appl. Phys. Lett. 87, 211109 2005 and J Y Kim, B Yellampalle, G Rodriguez, R D Averitt, A J Taylor, J H Glownia, Appl. Phys. Lett., 88, 041123 2006);

Spatial coding/decoding, which consists of encoding/decoding the temporal profile of the terahertz radiation on the diameter of the sensor pulse signal (J Shan, A S Weling, E Knoesel, L Bartels, M Bonn, A Nahata, G A Reider, T F Heinz, Opt. Lett. 25, 426 2000): S P Jamison, J Shen, A M MacLeod, W A Gillespie, D A Jaroszynski, Opt. Let. 28, 1710 2003 and K Y Kim, B Yellampalle, A J Taylor, G Rodriguez, J H Glownia, Opt. Lett. 32, 1968 2-7 and references cited in the last article).

These devices dispense with the temporal resolution limit of spectral decoding and enable single-shot diagnosis of terahertz pulses of short duration. However, none of these spatial solutions is applicable for the measurement of pulses with a duration greater than a few picoseconds. In addition, these novel single-shot methods are difficult to implement, in terms of beam alignment, and little suited to the context of terahertz imaging.

Another important limitation to the existing single-shot solutions stems from decoding by means of crossed polarisers, i.e. by placing the electro-optical medium between two polarisers oriented so that the sensor is not transmitted in the absence of an electromagnetic field. This form of detection implies a non-linear response of the signal according to the phase delay amplitude. In the majority of applications, the analyser is intentionally oriented so as to collect an almost zero optical bias and obtain an additional term in the response function so as to measure the bipolarity of the electro-optical signals.

The response function is then defined by the following equation $F_1$, valid for small phase delays such that $\Gamma+\Gamma_0<0.5$ rad:

$$I_{signal}=I_0 \cdot (\Gamma^2+2\Gamma \cdot \Gamma_0+\Gamma_0^2), \text{ where} \qquad (F_1)$$

$I_{signal}$ is the intensity of the signal measured;
$I_0$ is the intensity of the sensor signal;
$\Gamma$ is the phase delay resulting from the birefringence induced; and
$\Gamma_0$ is the optical bias, or phase delay measured in the absence of induced birefringence.

The case described by equation $F_1$ can be simplified using a detection of the lock-in type, and it is thus possible to dispense with the term $\Gamma_0^2$. Nevertheless, even in this simplified case, currently almost inconceivable for a single-shot detection, the prior art shows that the measured signal comprises distortions and artefacts (Z Jiang, F G Sun, Q Chen, Appl. Phys. Lett. 74, 1191 1999; Y Li, Appl. Phys. Lett. 88, 251108 2006). These distortions cannot in general be corrected without knowledge of the characteristics of the electromagnetic field to be characterised, characteristics of the sensor signal $I_0$ and fluctuations in the time delay between these two pulses. In addition, because of the dependence of the measured signal $I_{signal}$ with the intensity of the sensor signal $I_0$ and the optical bias $\Gamma_0$, the encoded signal is also perturbed along the Gaussian intensity profile of the sensor pulse.

One of the important fields of application of single-shot measurement of terahertz radiation concerns the field of terahertz spectroscopy in the temporal domain. According to this analysis technique, it is sought to characterise for example the absorption properties of an optical medium in the terahertz frequency range. For this purpose, the measurement method consists of making two acquisitions of the profile of the terahertz pulse, with and without optical medium. However, this measurement method is perturbed by fluctuations in the terahertz pulse source that limits the sensitivity thereof (S P Mickana, K-S Leeb, T-M Lub, J Munch, D Abbotta, X-C Zhang, Microelectronics Journal 33, 1033 2002).

Single-shot measurement techniques are all based on the use of a laser source with brief pulses, the duration of which is situated typically in the picosecond (ps) and femtosecond (fs) range. The performance of single-shot devices according to the methods described above are then directly related to the characteristics of these pulses such as the spectrum and duration thereof but also the spatial and temporal stability thereof.

In addition, the sources of intense terahertz radiation, both current and in development, or the new-generation particle accelerators, are based mainly on the use of pulsed laser sources in the fs/ps range, the characteristics of which are adapted for these radiation or particle sources. In the majority of cases, the characteristics of the pulses delivered by these laser sources are therefore ill suited to use of the single-shot methods described above. There exists currently on the market a wide competing range of pulsed lasers that can be used for the generation of terahertz radiation or the acceleration of particles, but where the characteristics of the pulses delivered differ.

SUMMARY OF THE INVENTION

The present invention aims to overcome these drawbacks of the prior art by proposing a method and device for single-shot measurement, based on the principle of spectral coding/decoding, which are compatible with all brief pulse laser sources (UV-NIR), and capable of functioning over a wide terahertz frequency range, for example 0.01-20 terahertz.

The invention aims in particular to measure the phase delay caused in the perturbed optical medium, in an absolute manner (amplitude and sign) and non-deformed, that is to say that is independent of the amplitude of this phase delay, and the characteristics of the pulse-type optical signal on which this phase delay is encoded.

In addition, the invention aims to produce a single-shot device capable of detecting a phase delay of less than 5 mrad, over the whole of the spectral analysis window.

The invention described below proposes to concentrate at least part of the energy of a pulsed optical signal, delivered by a laser, so as to generate a supercontinuum on which the variation in birefringence of an optical medium through which a terahertz perturbation passes is then encoded.

The invention then makes provision for calculating the phase delay caused by the terahertz perturbation by means of the measurement of the ellipticity of the polarisation of the supercontinuum according to a simultaneous detection configuration.

In this regard, the invention concerns, in its most general acceptance, a method for the single-shot measurement of the transient birefringence caused in an optical medium 12 by at least one terahertz perturbation 6, the method comprising a step of emission and spectral coding of a pulsed optical signal 2. The coding step, which comprises the generation of a supercontinuum 3, is also combined with a step of decoding the polarisation ellipticity of the supercontinuum induced by the perturbation 6 of the medium 12, by decomposing the electrical field of the supercontinuum in two polarisation directions and simultaneously measuring the intensities $I_s$ and $I_p$ of the two components.

According to particular embodiments:
the method comprises a step of balancing the intensities $I_s$ and $I_p$ of the two components of the electrical field of the supercontinuum;
the step of generating the supercontinuum has a phase of propagation of at least part of the pulsed optical signal in a monofilament mode in order to be free of the spectral and temporal characteristics of the pulsed optical signal;
the method comprises at least one step of optical compensation by correction of the chromatic and spatial aberrations of the device;
the coding step comprises a temporal shaping step comprising a phase of stretching the supercontinuum consisting of propagating the supercontinuum along an identical geometrical path for all the wavelengths of the supercontinuum;
the method comprises a step of shaping the spectral, spatial and temporal distribution of the supercontinuum; and/or
the method comprises:
i. a step of spatial separation of the terahertz perturbation into two analysis and reference terahertz perturbations;
ii. a step of temporal offsetting of the two analysis and reference terahertz perturbations; and
iii. a step of encoding the two analysis reference terahertz perturbations on a pulse of the supercontinuum.

The invention also concerns a device for single-shot measurement of the transient birefringence induced in an optical medium by at least one terahertz perturbation, the device comprising a source emitting a pulsed optical signal and means of spectral coding of the pulsed optical signal. The spectral coding means, which comprise means of generating a supercontinuum, are combined, by means of decomposing the electrical field of the supercontinuum in two polarisation directions S and P, with a unit for simultaneous measurement of the intensities $I_s$ and $I_p$ of the two components.

According to particular embodiments:

the means of generating the supercontinuum comprise means of forming a monofilament in order to be free of the spatial and temporal characteristics of the pulsed optical source;

the device comprising means of focussing the optical pulses in order to concentrate part of the energy until it reaches the propagation threshold according to a monofilament mode in a non-linear medium;

the device comprising means of focussing the optical pulses so as to inject some of these pulses into an optical fibre;

the device comprising at least one focussing means and a diaphragm placed on the optical path of the pulse in order to attenuate the effects of spatial fluctuations on the generation of the supercontinuum;

the decomposition means comprise balancing elements;

the balancing elements consist of a quarter-wave plate associated with a polariser;

the decomposition means comprise means of correcting the chromatic and spatial aberrations of the device;

the decomposition means comprise two secondary polarising splitting plates respectively disposed on the optical path of the two components of the supercontinuum and each having a function opposite to that of the polariser;

the generation means have means of adapting the supercontinuum consisting of dispersive optical elements for controlling the temporal stretching of the supercontinuum;

at least one of the two components of the electrical field of the supercontinuum 3 is propagated towards a spectrograph by means of at least one optical fibre; and/or the device also comprises means 50) of spatial separation of the terahertz perturbation 6 into two analysis 6a and reference 6b terahertz perturbations and means 52 for the temporal offsetting of one of the two analysis 6a and reference 6b terahertz perturbations.

According to another aspect, the invention concerns the use of a device according to the invention:

for terahertz spectroscopy; or for diagnosing beams of charged and accelerated particles.

The combination of the generation of the supercontinuum and simultaneous detection makes it possible to obtain a direct and non-deformed measurement of the transient birefringence variation with uniform sensitivity over the whole of the temporal analysis window and solely limited by the shot noise.

This is because generating a supercontinuum from the pulsed optical signal makes it possible to decouple the measurement device from the characteristics of the pulsed optical signal. Moreover, the supercontinuum can be generated so as to have a spectral intensity distribution that is substantially flat over the detection window, which improves the quality of the measurement by obtaining a signal to noise ratio that is constant over said temporal window.

This homogenisation of the analysis window can be done directly when the supercontinuum is generated and can also be the subject of a supplementary step after the supercontinuum is generated by means of passive or active optical elements according to the degree of homogenisation required.

Moreover, the simultaneous and balanced detection of the intensity of the components of the supercontinuum is advantageous in that it makes it possible to eliminate the fluctuations in intensity of the sensor pulse signal. Balanced detection also makes it possible to obtain directly the amplitude and sign of the phase delay induced, without errors due to crossed polarisers. Applied to the characterisation of a terahertz perturbation, this balanced detection makes it possible to find the value of the terahertz electromagnetic field in an optical medium.

Carrying out a shot by shot wide-band balanced detection makes it possible to measure the transient birefringence variation under conditions solely limited by the shot noise of the detector.

The use of polarising splitting plates advantageously minimises chromatic spatial faults. The use of means for compensating for residual chromatic faults improves the stability of the balancing of the components of the electrical field of the pulsed sensor signal vis-à-vis spatial fluctuations of the supercontinuum.

The fact that the device measuring the ellipticity comprises two optical fibres also makes it possible to be free of the spatial fluctuations on the entry slot of the spectrograph.

Finally, generating, from the terahertz perturbation, two terahertz perturbations offset in time with respect to each other and encoding them on two distinct parts of the spectrum of the supercontinuum simultaneously makes it possible to be free of the fluctuations of the terahertz source employed.

Thus the method and device according to the invention are compatible with all short pulsed laser sources (UV-NIR) and the performance of the measurement is independent of the pulsed laser source used. In addition, the sensitivity of the device is limited only by the shot noise, and the temporal analysis window can be continuously adapted between 0.01 and 20 THz with better temporal resolution than that of the devices of the prior art and a sensitivity at least equal.

BRIEF DESCRIPTION OF THE DRAWINGS

Other features and advantages of the invention will emerge from the following reading of detailed example embodiments, with reference to the figures, which show respectively.

DETAILED DESCRIPTION OF THE PREFERRED EMBODIMENTS

Although the following description refers mainly to electromagnetic fields, it is understood that the measurement method and device according to the invention can be used for measuring the birefringence variation independently of the nature of the perturbation inducing this transient birefringence in the terahertz range. In particular, the terahertz perturbation can be induced by an acoustic wave, a shock by a laser pulse, etc.

Because of this, the term terahertz perturbation refers to any type of electromagnetic field, acoustic wave or other perturbation within the terahertz frequency range.

Moreover, the term optical medium used below refers to any physical medium (solid, liquid or gas) liable to present birefringence induced by an external perturbation.

In addition, coding by polarisation modulation induced by the birefringence of the optical medium is described below in the particular case of the supercontinuum passing through the optical medium. However, without departing from the scope of the invention, the method and device also apply to any other polarisation modulation means such as for example reflection on the surface of the optical medium.

The words generation of the supercontinuum relate to the well known process that consists of modifying, by various non-linear processes, the spectral profile of intensity $I(\lambda)$ of an optical pulse so as to obtain a very pronounced spectral broadening. There exist a great variety of methods for generating supercontinua with also varied characteristics. The following description of example embodiments of the invention describes a few advantageous generation modes in the context of the invention.

In addition, the supercontinuum being, in this context, used as a means for producing a device compatible with all pulsed laser sources, the term supercontinuum extends to all processes of amplifying part of the spectrum of said supercontinuum without departing from the scope of the invention.

The measurement method according to the invention will now be described with reference to a first example embodiment shown in FIG. 1.

In this example embodiment, an optical medium 12 is subjected to a terahertz perturbation 6, in the form of a terahertz electromagnetic field. Under the effect of this terahertz electromagnetic field 6, the birefringence of the optical medium 12 is modified. A transient regime is then established in the optical medium 12, during which the optical medium 12 has a transient birefringence characterised by two orthogonal optical axes (or neutral lines) with optical indices $n_e (\lambda,t)$ and $n_o (\lambda,t)$ with $\lambda$ and t representing respectively the wavelength and the time.

According to a first example embodiment, the measurement method according to the invention comprises a first step of emitting a pulsed optical signal 2 from an optical source 14, such as a laser source of ultra-short pulses in the time range of femtoseconds (fs) or picoseconds (ps). This source of optical pulses 14 is synchronised with the terahertz perturbation 6.

The pulsed optical signal 2 propagates through means 4 of generating a supercontinuum 3. Thus part of the energy of the pulsed optical signal 2 is injected by focussing means 17 into a non-linear material 18, such as a sapphire substrate, so as to achieve the necessary intensity sufficient for the pulsed optical signal 2 to propagate in the non-linear material 18 in order to interact effectively with said non-linear material 18, according to non-linear processes. Thus part of the pulsed optical signal 2 is converted into a supercontinuum 3.

Advantageously, the means 4 of generating the supercontinuum 3 also comprise means 19 of adapting the supercontinuum 3. Thus the supercontinuum 3 is collimated and its temporal stretching is adapted to a predetermined analysis window by means of dispersive optical elements.

The supercontinuum 3 is also polarised linearly by polarisation means 20, and the polarisation thereof is oriented so that traversing the optical medium 12 perturbed by the terahertz perturbation 6 converts the linear polarisation into an elliptical polarisation.

According to one variant (not shown), the generation of the supercontinuum 3 is effected in the pulsed optical source 14. This is for example the case when so-called white lasers are used.

The supercontinuum 3 is then propagated in a perturbed part of the optical medium 12 so as to sound the transient birefringence induced by the terahertz perturbation 6. The time delay between the supercontinuum 3 and the terahertz perturbation is adjusted so the two signals overlap in time in the optical medium 12.

Advantageously, the spectral distribution of intensity of the supercontinuum 3 is adjusted so as to present a substantially flat profile. This homogenisation of the analysis window can be done directly when the supercontinuum 3 is generated, and can also advantageously be the subject of an additional step after the supercontinuum is generated by means of passive or active optical elements according to the degree of homogenisation required.

The method then comprises a step of spectral decoding by measurement of the ellipticity for each wavelength of the supercontinuum 3. In the absence of a perturbation, the linear polarisation of the electrical field of the supercontinuum 3, at the output of the optical medium 12, is transformed into a circular polarisation via polarisation means 32. Next the electrical field of the supercontinuum 3 is decomposed simultaneously in two orthogonal polarisation directions denoted P and S.

In theory, this decomposition of the polarisation of the supercontinuum 3 should make it possible to obtain a balanced detection, that is to say for which the intensities $I_s$ and $I_p$ of the two components of the electrical field of the supercontinuum 3 in the two polarisation directions S and P are equal for all wavelengths, in the absence of terahertz radiation 6.

However, the properties of the optical elements are such that perfect balancing is impossible to achieve over the spectral width of the supercontinuum 6. This introduces a bias in the measurement of the ellipticity that limits the sensitivity of the device if it fluctuates shot by shot.

According to the method of the invention, the shot by shot variations of balancing are minimised. The balancing step comprises in effect a phase of compensation of the chromatic faults of the device.

The step of simultaneous measurement of the intensities $I_p$ and $I_s$ of the two components of the two components of the electrical field of the supercontinuum 3 makes it possible to deduce the transient variation in birefringence and, depending on the application, the characteristics of the terahertz perturbation 6 (intensity, temporal profile, etc) and information on the optical medium 12 perturbed.

Figure 1:
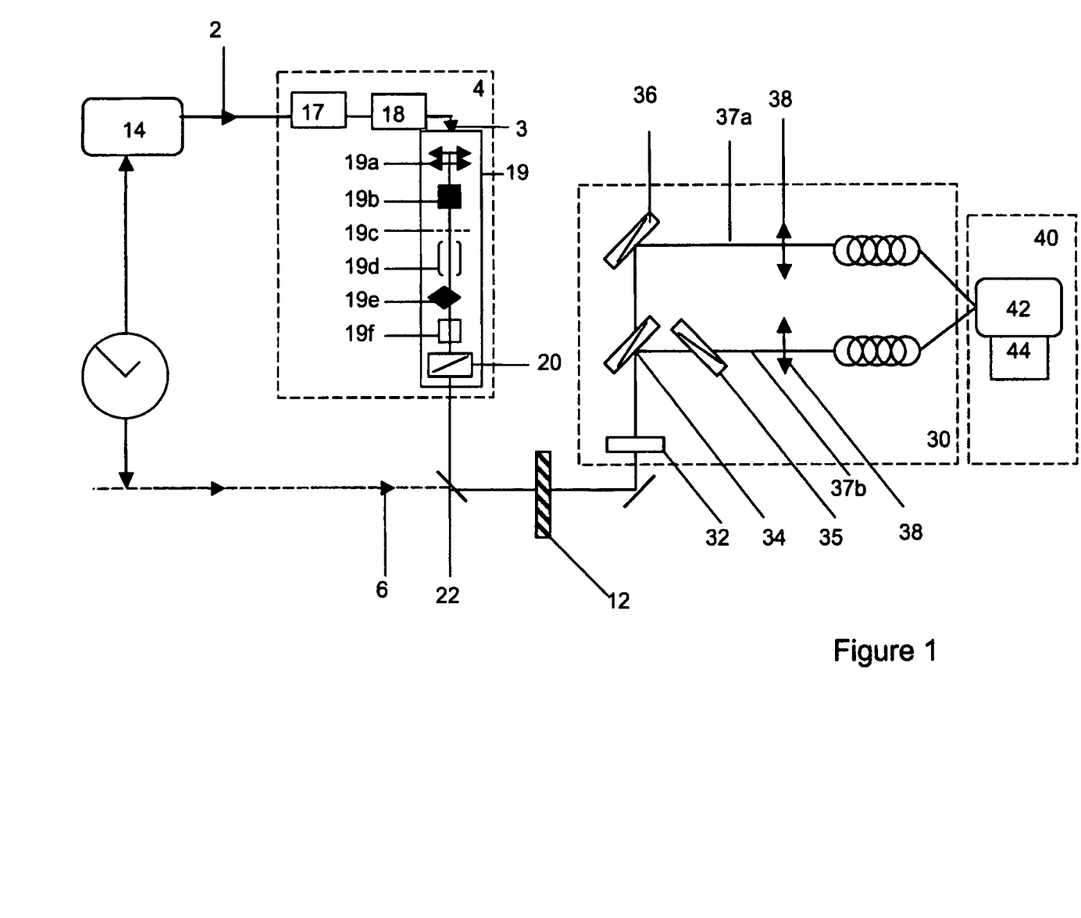
FIG. 1, a schematic representation of a first example embodiment of a device according to the invention.

FIG. 1 illustrates more particularly an example of a measuring device implementing the above method.

In this first example embodiment, the terahertz perturbation 6, here a terahertz electrical field, is produced by a pulse of relativistic electrons with a duration of a few picoseconds, delivered by an accelerator phototriggered by a source of optical pulses 14, in this case a femtosecond laser.

The source of optical pulses 14 consists of an amplified Ti:Sa laser source that delivers a pulsed optical signal 2 of 160 femtoseconds having a wavelength of 790 nanometres. The optical pulse source 14 is synchronised on the accelerating radio-frequency wave of the packet of relativistic electrons composing the terahertz perturbation 6 by slaving of the length of the laser cavity of the oscillator of the optical pulse source 14. The synchronisation between the pulse of relativistic electrons composing the terahertz perturbation 6 and the source of optical pulses 14 is approximately 1 ps.

In this example embodiment, the perturbed optical medium 12 is a Zn:Te crystal. It is then sought to characterise the effect of the passage of the electron beam in the vicinity of this optical medium 12, that is to say to measure the birefringence induced in the Zn:Te crystal by the electrical field of the relativistic electrons and the terahertz perturbation generated when said beam of electrons passes through a sheet of metal.

The optical medium 12 is cut along the plane 110) and placed at approximately 3-4 mm from the propagation axis of the electron beam. Under these conditions, the electrical field of the relativistic electrons and therefore the terahertz perturbation 6 is in the plane 110) of the Zn:Te crystal. The result is a birefringence induced in the optical medium 12 characterised by two optical axes in the plane 110) and oriented at 45 degrees with respect to the direction [001]. The terahertz perturbation 6 is an electromagnetic field that passes through the optical medium 12 and also induces a transient birefringence.

The device according to the invention also comprises means 4 of generating a supercontinuum 3 polarised linearly, from the pulsed optical signal 2 emitted by the source of optical pulses 14. Advantageously, the pulsed optical signal 2 lies within the ultraviolet range as far as the near infrared.

The supercontinuum generation means 4 consist of focussing means 17 for adapting the beam of the pulsed optical signal 2 so as to reach a monofilament in the non-linear medium 18. The traverse of the non-linear medium 18 comprises a part during which the propagation takes place in a monofilament and generates a supercontinuum 3 from the pulsed optical signal. At the exit from the non-linear medium 18, the intensity of the supercontinuum 3 and the spatial, spectral and temporal distribution thereof are adapted to the characteristics of the terahertz perturbation 6 by adaptation means 19.

According to the first example embodiment, the focussing means 17 comprise a lens, a diaphragm and a filter of variable intensity. Moreover, the non-linear medium 18 is a sapphire 3 millimetres thick, the optical axis of which is oriented perpendicular to the surface thereof. The focussing means 17 and the non-linear medium 18 are adjusted so that 1 μJ of the pulsed optical signal 2 attains, in the non-linear medium 18, an intensity of around $10^{11}$ W/cm$^2$ corresponding to the autofocussing threshold, focussing with a numerical aperture of less than 0.1.

According to the characteristics of the optical pulse source 14 (peak power, wavelength, spatial mode), the non-linear medium 18 and the focussing means 17 can always be adapted so as to obtain a length for which the interaction between the pulsed optical signal 2 and the non-linear medium 18 is sufficient to generate a supercontinuum 3. Thus a supercontinuum 3 can for example be generated from a few nJ of a pulsed optical signal 2 propagated in the core of an optical fibre, including in photon crystal fibres.

The means 19 of adapting the characteristics of the supercontinuum 3 advantageously comprise a collimation lens 19a, as well as passive or active elements 19b for adapting the spectrum of the supercontinuum 3 to the variation in birefringence to be measured.

Advantageously, the adaptation means 19 also comprise a low-pass dielectric filter 19c and possibly an active device 19d capable of modifying the spectral and temporal profile of the supercontinuum 3.

The adaptation means 19 also possibly comprise a step of optical amplification of part or all of the supercontinuum 3 by means of amplification elements 19e well known to persons skilled in the art.

Finally, the means 19 of adaptation of the supercontinuum 3 advantageously comprise a stretcher or compressor 19f by frequency drift of the duration of the supercontinuum 3.

According to one embodiment, the supercontinuum 3 is collimated by means of an achromatic lens that is responsible for the majority of the dispersion on the optical path between the non-linear medium 18 and the optical medium 12. The spectral stretching between 460 and 760 nm is then $T_c$–2.25 ps, with a pulse duration obtained by Fourier transformation of the spectrum equal to $T_0$=4.4 fs, $T_{min}$=100 fs, according to equation $F_1$.

According to another embodiment, the supercontinuum 3 is preferably stretched by two passages in 20 cm of the SF57, which results in a stretching $T_c$=60 ps over the spectral width transmitted by a Zn:Te crystal 550-730 nm). The Fourier transform of the spectral distribution is equivalent to a pulse duration $T_0$=6.6 fs. Under these conditions $T_{min}$=630 fs.

The adaptation means 19 also comprise a polariser 20 for linearly polarising the supercontinuum 3 before being directed by propagation means 22 to the optical medium 12.

The optical path of the supercontinuum has an adapted length so that it passes through the optical medium 12 at the moment of the transient birefringence induced by the terahertz perturbation 6.

It should be noted that the direction of the polarisation of the supercontinuum 3 is adapted to the orientation of the optical axes characterising the transient birefringence of the optical medium 12 so that said birefringence converts the linear polarisation of the supercontinuum into an elliptical polarisation.

In this example embodiment, the supercontinuum 3 passes through the optical medium 12, perpendicular to the plane 110) of the crystal, the axis [001] being orthogonal to the direction k of propagation of the supercontinuum 3. The transient birefringence of the optical medium 12 is then characterised by two optical axes in the plane 110). The direction of polarisation of the supercontinuum 3 is advantageously at 45 degrees from said optical axes.

The birefringence induced by the terahertz perturbation 6 in the optical medium 12 converts the linear polarisation of the supercontinuum 3 into an elliptical polarisation. The phase difference, denoted $\Gamma(\lambda)$, between the two components of the electrical field of the sensor pulse signal, on the two principal axes of the induced birefringence, then depends on the spectral components of the supercontinuum 3.

The device according to the first example embodiment also comprises means of decoding by decomposition and measurement of the ellipticity of the supercontinuum.

The decomposition means 30 consist of a quarter-wave plate 32, a first polarising splitting plate 34, two secondary polarising splitting plates 35, 36, and two achromatic lenses 38.

The quarter-wave plate 32, optimised for the visible range 450-800 nanometres), is placed and oriented so as to convert the rectilinear polarisation of the supercontinuum 3, in the absence of terahertz perturbation 6, into a circular polarisation.

The supercontinuum 3 is then propagated towards a first polarising splitting plate 34 that decomposes its electrical field in two perpendicular polarisations S and P. The secondary polarising splitting plates 35 and 36 are then placed respectively on the optical paths 37a and 37b of the two decomposed beams, so that each component is once transmitted by the plate 34 and then reflected by the secondary polarising plate 36, or once reflected by the plate 34 and then transmitted by the secondary polarising plate 35. Under these conditions, each beam finally undergoes the same optical transformations. Thus the chromatic faults due the polarisers are corrected by compensation.

Preferably, the first polarising splitting plate 34 and the secondary polarising splitting plates 35, 36 consist of metal grilles deposited on thin substrates, which guarantees a high uniform extinction coefficient in the visible range while preventing deviation of the beam on its wavelength.

The intensities $I_s$ and $I_p$ of each wavelength are then measured in a measurement unit 40. The measurement unit 40 consists of at least a spectrograph 42 and a multichannel detector 44. The intensity $I_p(\lambda)$ and $I_s(\lambda)$ of the two components of the supercontinuum 3 are then detected simultaneously for each pulse of the supercontinuum 3.

Advantageously, the two components of the supercontinuum 3 are coupled by means of optical fibres that provide the positioning on the entry slot of the spectrograph 42 and the offset of the measurement unit.

From the measurement performed by the spectrograph, it is possible to deduce the phase delay between the two components of the electrical field $\Gamma(\lambda)$ of the supercontinuum by means of the following equation F2:

$$\sin \Gamma(\lambda) = (Ip(\lambda) - I_s(\lambda))/I_p(\lambda) + I_s(\lambda)) \quad \text{(F2)}$$

The variation in the birefringence as a function of the time $\Gamma(t)$ is deduced directly from the knowledge of the spectral stretching of the supercontinuum 3.

According to a variant, the two components of the supercontinuum 3 are focussed after the secondary polarising splitting plates 35, 36 in an assembly of optical fibres composed of two silica fibres with a diameter of 400 μm, one of the ends of which is positioned on the entry slot of a spectrograph. The spectral resolution of the device is 1 nm. The spectra are recorded by means of a CCD camera. The shot by shot stability of the balancing obtained under these conditions is illustrated in FIG. 3b below.

Figure 2:
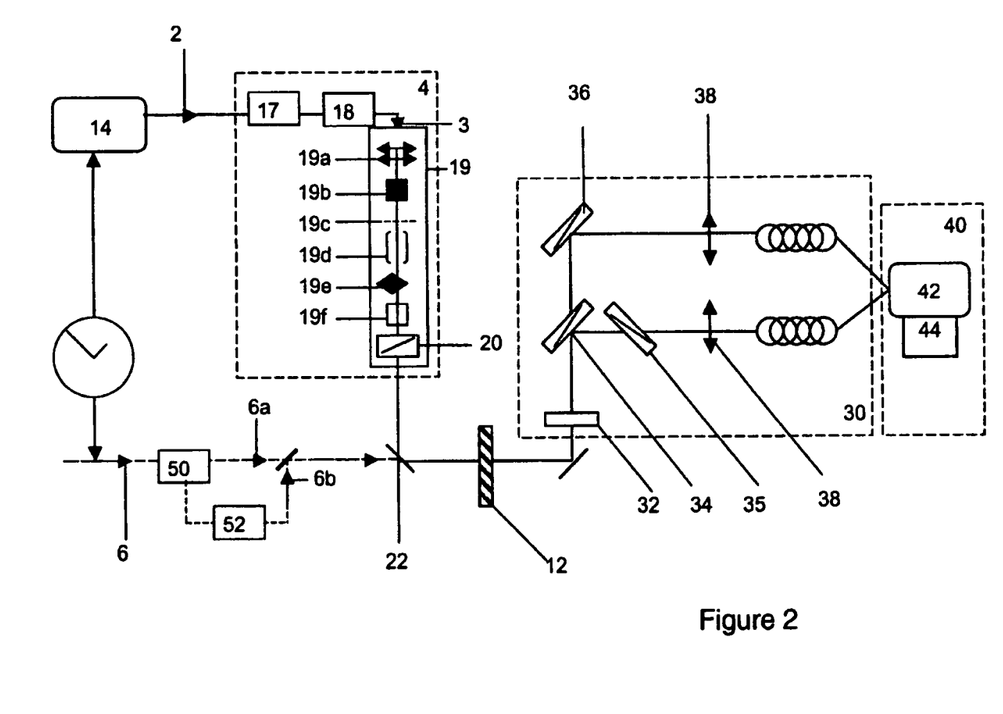
FIG. 2, a schematic representation of a second example embodiment of a device according to the invention.

A second example embodiment of a measurement device according to the invention will now be described with reference to FIG. 2.

In this example embodiment, firstly, a first terahertz electromagnetic field, called an analysis terahertz perturbation 6a, and a second terahertz electromagnetic field, called a reference terahertz perturbation 6b, are generated from the terahertz perturbation 6. The intensity of the electromagnetic field of the reference terahertz perturbation 6b is proportional to the intensity of the electromagnetic field of the analysis terahertz perturbation 6a before the optical medium 12.

Thus, firstly, two analysis 6a and reference 6b terahertz perturbations are created from a single initial terahertz pulse and then offset in time. To do this, an initial perturbation 6 is decomposed, by spatial separation means 50, into two beams corresponding to the analysis 6a and reference 6b terahertz perturbations. The beam corresponding to the reference terahertz perturbation 6b is propagated through the optical medium 12 to be characterised.

Moreover, the optical delay between the beams 6a, 6b is adapted, by delay means 52, disposed on the optical path of the analysis 6a or reference 6b terahertz perturbations, so as to offset in time the two beams 6a and 6b. Thus these two beams are propagated in the optical medium 12 and encoded successively on the same pulse of the supercontinuum 3.

Secondly, the two analysis 6a and reference 6b terahertz perturbations are encoded on two distinct parts of the spectrum of the supercontinuum 3 and the profile of the two analysis 6a and reference 6b terahertz perturbations is detected, in a single shot according to the method previously described. The reference perturbation 6b makes it possible to correct the shot by shot fluctuations of the terahertz source.

According to an alternative embodiment, the analysis 6a and reference 6b terahertz perturbations are generated from a beam of accelerated electrons. To do this, a sheet of metal, or any other element making it possible to generate a transition radiation, is disposed on the path of the beam of accelerated electrons.

Thus the terahertz electromagnetic field generated constitutes the analysis terahertz perturbation 6a while the electrical field of the electrons constitutes the reference terahertz perturbations 6b. The analysis terahertz perturbation 6a is delayed by means of a dispersive substrate 52. Then the beams corresponding to the analysis 6a and reference 6b terahertz perturbations are propagated as before in the optical medium 12 to be characterised so as to induce a transient birefringence in the optical medium 12, detected in the same way as before.

Figure 3A:
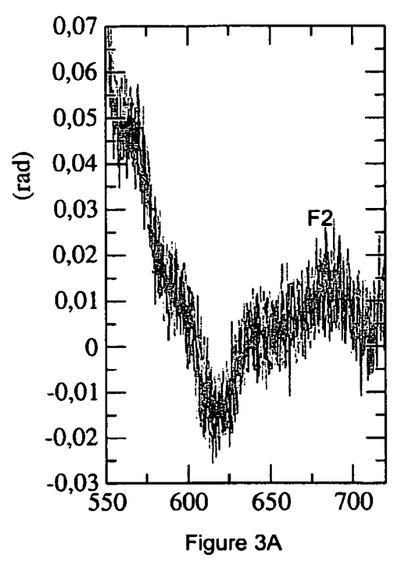
FIGS. 3a to 3c, measurements revealing the stability and sensitivity of a device according to the invention.
Figure 3B:
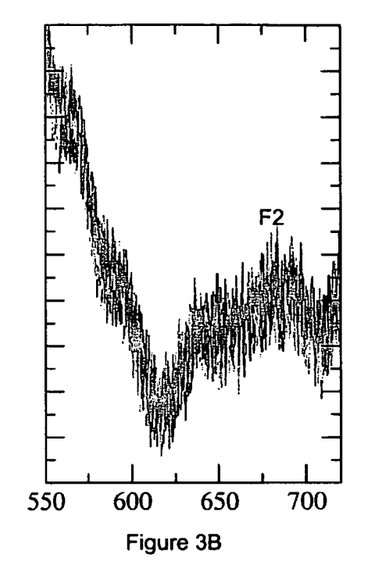
Figure 3C:
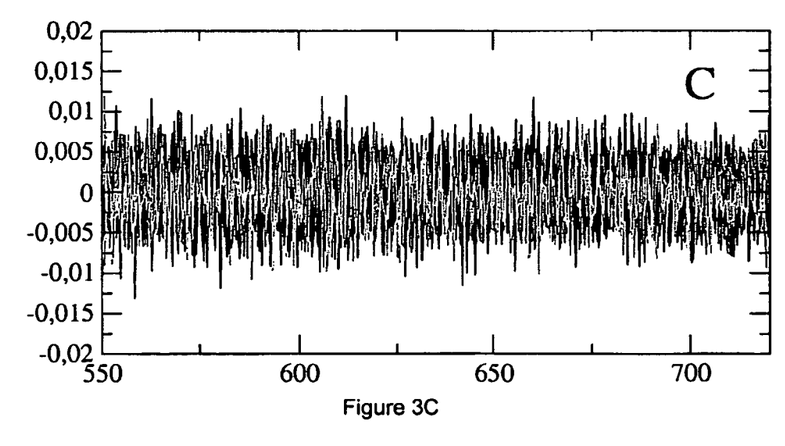

FIGS. 3A to 3C represent measurements revealing the stability and sensitivity of a device according to the invention.

FIG. 3A shows the signal $F_2$, in the absence of any terahertz radiation, recorded on 20 consecutive pulses of the pulsed optical signal 2, at the rate 10 Hz. FIG. 3B illustrates the same measurement 15 minutes later.

FIG. 3C shows the shot by shot fluctuations calculated with respect to the mean of 20 consecutive sensor pulses and clearly shows the stability of the device according to the invention.

Figure 4:
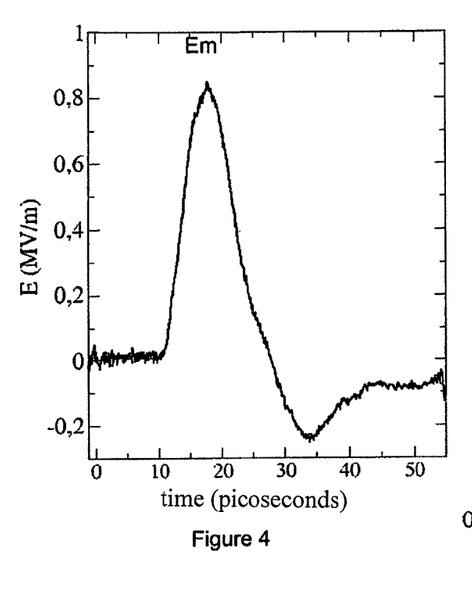
FIG. 4, a one-shot recording of the temporal profile of the electrical field induced in a Zn:Te crystal.

The electrical field in the optical medium 12 can be calculated from the absolute measurement of the phase delay. For the case considered in this embodiment, the electrical field is deduced from the phase by equation F3 where:

$$\Gamma(\lambda) = 2 \cdot \pi \cdot d \cdot n^3(\lambda) \cdot \Gamma_{41} \cdot E(\lambda)/\lambda, \text{ where}$$

d is the thickness of the optical medium 12 of a Zn:Te crystal;

$n(\lambda)$ is the optical index of the optical medium 12;

$\Gamma_{41}$ is the electro-optical coefficient of the optical medium 12 ($= 4.25 \times 10^{-12}$ m/W);

E is the electrical field; and $\lambda$ is the wavelength,

In FIG. 4, a one-shot recording Em of the temporal profile of the electrical field induced in a Zn:Te crystal with a thickness of 0.5 mm by a packet of relativistic electrons of 8 MeV propagating in the vicinity of this crystal.

Figure 5:
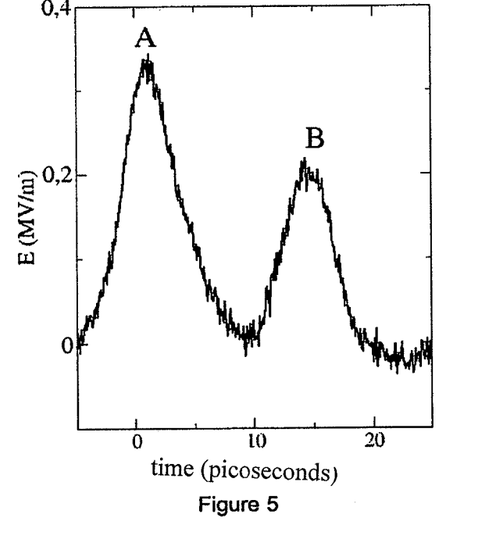
FIG. 5, a one-shot recording of the temporal profile of the electrical field of a packet of electrons and a terahertz electromagnetic field offset in time.

FIG. 5 also illustrates a one-shot recording of the temporal profile of the electrical field of a packet of electrons A and a terahertz electromagnetic field B offset in time and encoded on two distinct supercontinuum parts.

The invention is not limited to the example embodiments described and shown. It is understood that a person skilled in the art is in a position to implement different variants of the invention without departing from the scope of the patent.

For example, the measurement device and method according to the invention could be used for characterising ultrabrief optical sources.

The invention claimed is:

1. Method for the one-shot measurement of the transient birefringence induced in an optical medium (12) by at least one terahertz perturbation (6), the method comprising a step of emission and spectral coding of a pulsed optical signal (2), characterised in that the coding step, which comprises the generation of a supercontinuum (3), is combined with a step of decoding the polarisation ellipticity of the supercontinuum induced by the perturbation (6) of the medium (12), by decomposition of the electrical field of the supercontinuum in two polarisation directions and simultaneous measurement of the intensities $I_s$ and $I_p$ of the two components, the one-shot measurement consisting of encoding the temporal profile of the terahertz perturbation on the spectral profile of a single pulse of the supercontinuum.

2. One-shot measurement method according to claim 1, also comprising a step of balancing the intensities $I_s$ and $I_p$ of the two components of the electrical field of the supercontinuum (3).

3. Measurement method according to claim 1, in which the step of generating the supercontinuum (3) has a phase of propagating at least part of the pulsed optical signal (2) in a monofilament mode in order to be free of the spectral and temporal characteristics of the pulsed optical signal (2).

4. Measurement method according to claim 1, comprising at least one step of optical compensation by correction of the chromatic and spatial aberrations of the device.

5. Measurement method according to claim 4, comprising a step of shaping the spectral, spatial and temporal distribution of the supercontinuum (3).

6. Measurement method according to claim 1, in which the coding step comprises a temporal shaping step comprising a phase of stretching the supercontinuum (3) consisting of propagating the supercontinuum (3) along an identical geometric path for all the wavelengths of the supercontinuum (3).

7. Measurement method according to claim 1, the method comprising:
   i. a step of spatial separation of the terahertz perturbation (6) into two analysis (6a) and reference (6b) analysis terahertz perturbations;
   ii. a step of temporal offset of the two analysis (6a) and reference (6b) terahertz perturbations; and
   iii. a step of encoding the two analysis (6a) and reference (6b) terahertz perturbations on a pulse of the supercontinuum (3).

8. Device for the one-shot measurement of the transient birefringence induced in an optical medium (12) by at least one terahertz perturbation (6), the device comprising a source (14) emitting a pulsed optical signal (2) and means (4, 12) for the spectral coding of the pulsed optical signal (2), characterised in that the spectral coding means (4, 12), which comprise means (4) of generating a supercontinuum (3), are combined, by means (30) of decomposing the electrical field of the supercontinuum in two polarisation directions S and P. with a unit (40) for the simultaneous measurement of the intensities $I_s$ and $I_p$ of the two components, the one-shot measurement consistin of encodin' the temporal profile of the terahertz perturbation on the spectral profile of a single pulse of the supercontinuum.

9. Device according to claim 8, in which the means (4) of generating the supercontinuum (3) comprise means (17, 18) of forming a monofilament in order to be free of the spatial and temporal characteristics of the pulsed optical source (14).

10. Measurement device according to claim 9, the device comprising means (17) of focussing the optical pulses (2) in order to concentrate part of the energy until it attains the propagation threshold according to a monofilament mode in a non-linear medium (18).

11. Measurement device according to claim 9, the device comprising means (17) of focussing the optical pulses (2) so as to inject some of these pulses into an optical fibre (18).

12. Measurement device according to claim 9, the device comprising at least one focussing means (17) and a diaphragm placed on the optical path of the pulse (2) in order to attenuate the effects of spatial fluctuations (2) on the generation of the supercontinuum (3).

13. Device according to claim 9, in which the decomposition means (30) comprise balancing elements (32, 34).

14. Device according to claim 13, in which the balancing elements consist of a quarter-wave plate (32) associated with a polariser (34).

15. Device according to claim 9, in which the decomposition means (30) comprise means (35, 36, 38) of correcting the chromatic and spatial aberrations of the device.

16. Device according to claim 9, in which the decomposition means (30) comprise two secondary polarising splitting plates (35. 36) respectively disposed on the optical path of the two components of the supercontinuum (3) and each have a function opposite to that of the polariser (34).

17. Device according to claim 9, in which the generation means (4) have means (19) of adapting the supercontinuum (3) consisting of dispersive optical elements for controlling the temporal stretching of the supercontinuum (3).

18. Device according to claim 9, in which at least one of the two components of the electrical field of the supercontinuum (3) is propagated towards a spectrograph by means of at least one optical fibre.

19. Device according to claim 8, the device also comprising means (50) of spatial separation of the terahertz perturbation (6) into two analysis (6a) and reference (6b) terahertz perturbations as well as means (52) for the temporal offsetting of one of the two analysis (6a) and reference (6b) terahertz perturbations.

20. A method for terahertz spectroscopy, said method comprising taking the one-shot measurement of the transient birefringence using the device of claim 8 and performing said terahertz spectroscopy from the one-shot measurement.

21. A method for diagnosis of beams of charged and accelerated particles, said method comprising taking the one-shot measurement of the transient birefringence using the device of claim 8 and performing said diagnosis from the one-shot measurement.

* * * * *